United States Patent [19]
Huang

[11] Patent Number: 5,279,315
[45] Date of Patent: Jan. 18, 1994

[54] DENTAL FLOSS ASSEMBLY

[76] Inventor: Ming-Liang Huang, No. 39-7, Ta-Tung Rd., Hsin-Ying City, Tainan County, Taiwan

[21] Appl. No.: 8,156

[22] Filed: Jan. 25, 1993

[51] Int. Cl.⁵ ............................................. A61C 15/00
[52] U.S. Cl. .................................... 132/324; 132/323
[58] Field of Search ................................. 132/323, 324

[56] References Cited

U.S. PATENT DOCUMENTS

| | | | |
|---|---|---|---|
| 3,913,597 | 10/1975 | Day | 132/324 |
| 4,162,687 | 7/1979 | Lorch | 132/323 |
| 4,671,307 | 6/1987 | Curbow et al. | 132/323 |
| 4,706,694 | 11/1987 | Lambert | 132/323 |
| 4,736,757 | 4/1988 | Badoux | 132/323 |
| 5,067,503 | 11/1991 | Stile | 132/323 |
| 5,125,424 | 6/1992 | Eisen | 132/323 |
| 5,127,415 | 7/1992 | Preciutti | 132/323 |

Primary Examiner—Gene Mancene
Assistant Examiner—Frank A. LaViola
Attorney, Agent, or Firm—Bacon & Thomas

[57] ABSTRACT

This invention relates to a dental floss assembly, which comprises a holder also for receiving the dental floss, a locating member mounted at the front portion of the holder, a holding member for dental floss which is mounted on the holding member and can be replaced. With a change in the angle of the holding member for dental floss by virtue of the locating member it is easy for the user to clean up dirts at the spaces between the teeth in deep cavity of the mouth so as to assure oral hygiene.

4 Claims, 5 Drawing Sheets

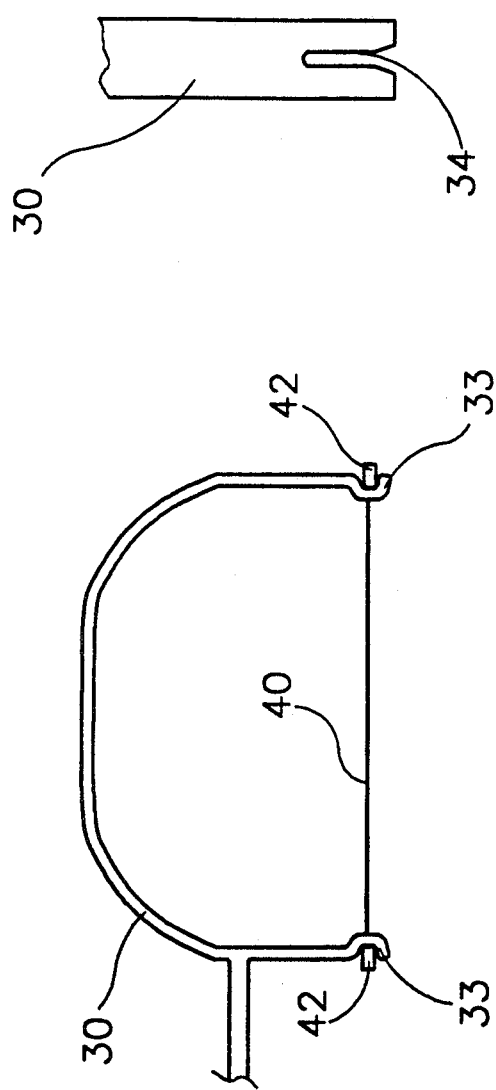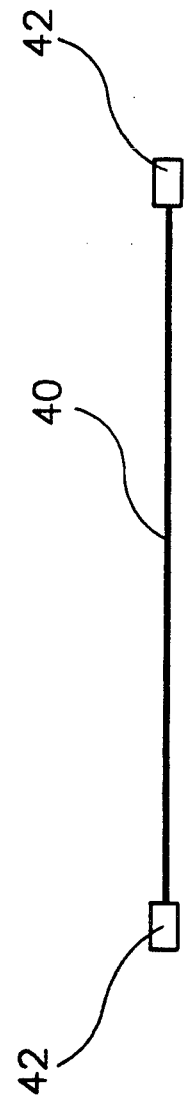

5,279,315

DENTAL FLOSS ASSEMBLY

FIELD OF THE INVENTION

This invention relates to a dental floss assembly that can change the angle of holding member of dental floss in facility of cleaning up the spaces between the teeth located deeper in the cavity of the mouth. Moreover it is rather convenient and economic for use as a result of easy replacement of new dental floss thereon.

BACKGROUND OF THE INVENTION

Among the conventional means of cleaning up the spaces between the teeth the dental floss is the most effective one to accomplish the result of cleaning up. However the conventional winding type dental floss is not convenient for use and can not be used in a graceful manner because the user has to grab it directly with fingers for cleaning up the teeth.

In order to overcome above-mentioned defects there comes up with dental floss rod on the market which relates to mount dental floss on a bow-shaped frame with a holder. It is more convenient than the winding type for use because the user only requires to grab the holder of the dental floss rod easily for cleaning up the spaces between the teeth thereof.

The dental floss rod as a whole resembles a straight line. However there are some teeth located much deeper in the cavity of the mouth where the spaces between the teeth located much deeper are irregular due to the relationship of teeth arranged. For this reason the dental floss rod is not liable to get deep access enough for cleaning up those spaces between the teeth in deep cavity of the mouth. While to solve the problem is to get the head of the dental floss rod bent so that it can be stretched deeply enough for easily inserting dental floss in each space between the teeth in deep cavity of the mouth. Nevertheless were the dental floss rod being bent it will easily get broken so that it has some defect in respect of use. In addition because the overall dental floss rod has to be disposed after use it also causes a great amount of waste and a problem of environmental protection.

SUMMARY OF THE INVENTION

Therefore it is an object of this invention to provide a dental floss assembly which can be changed in angle and stretched deeply for cleaning up the teeth in deep cavity of the mouth.

Another object is to provide a dental floss assembly which is easy for use and able to accomplish the purpose of oral hygiene.

Another object is to provide a dental floss assembly which is easy for the replacement of floss to meet the requirement of hygiene and rationalization.

These and other objects and advantages of this invention will become apparent to those skilled in the art after considering the following detailed specification together with the accompanying drawings.

BRIEF DESCRIPTION OF THE DRAWINGS

FIG. 6 is a local view of dental floss and its holding member showing another means of mounting the holding member for the dental floss.

FIG. 7 is an enlarged local side view of fastening portion of holding member for the dental floss shown in FIG. 6.

FIG. 8 is a plane view of the dental floss having solid block-type holding member.

DETAILED DESCRIPTION OF THE PREFERRED EMBODIMENTS

Figure 1:
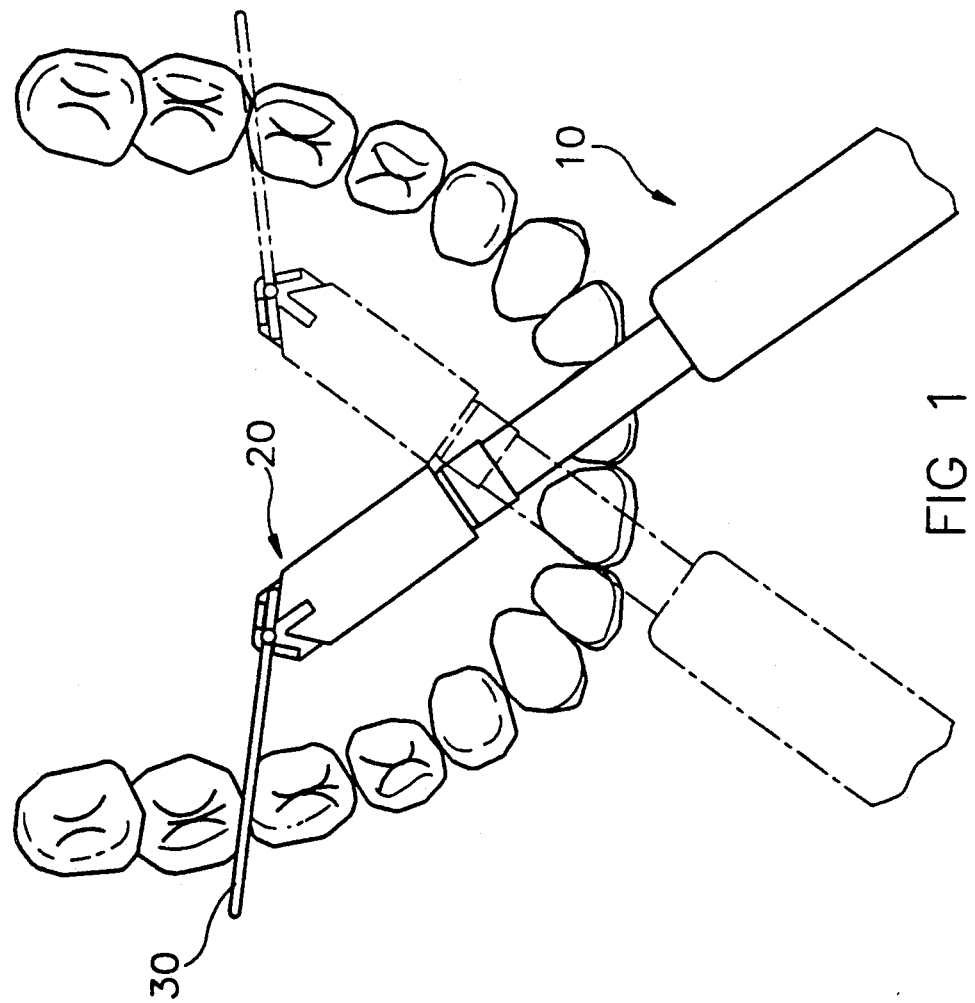
FIG. 1 is a perspective view of this invention in use.

Referring to FIG. 1 the present dental floss assembly comprises a holder 10, a locating member 20, a holding member 30 for a dental floss 40 which is movably mounted on the holding member 30. Wherein the holder 10 is provided for holding and holding member 30 together with locating member 20 are movably mounted thereon; and with the help of the locating member 20 the holding member 30 can be secured with the holder 10 to form a straight line or inclined toward the left or the right in facility of the holding member being stretched deeply into the cavity of the mouth whereby the dental floss is easily to reach the space between the teeth in the deep cavity of the mouth so as to meet the purpose of cleaning up the teeth thoroughly.

Figure 2:
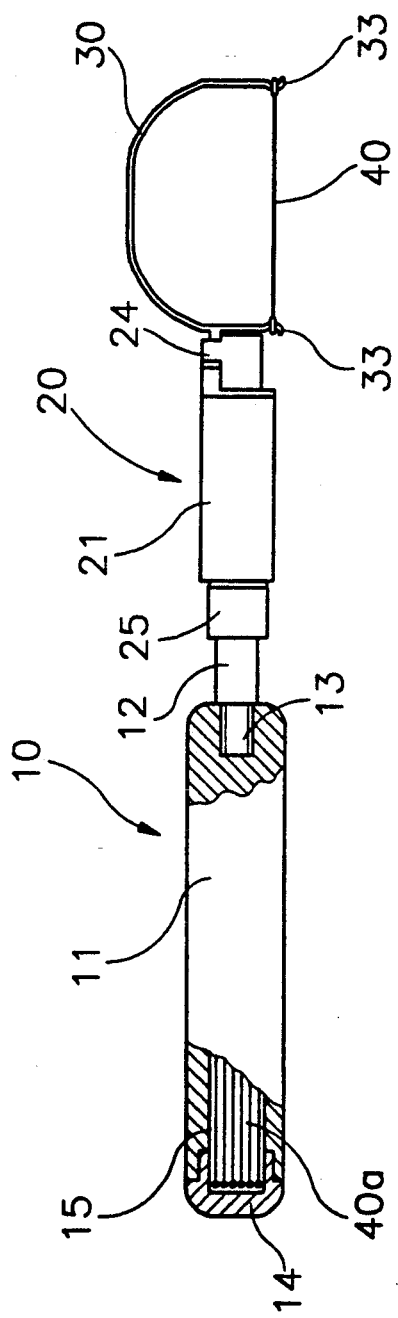
FIG. 2 is a partially side exploded view of this invention.

Referring to FIG. 2 the holder 10 is generally divided into a front portion and a rear portion of which the rear portion is thicker to form a holding portion 11 while the front portion is a thinner stem 12. The holding portion 11 has a hollow room 14 therein for receiving spare dental floss or accessories, and a cover 15 at its tail end and once the cover 15 is open the articles received in the room 14 can be withdrawn therefrom. The holding portion 11 has a junction 13 at its leading end and the junction 13 has internal thread therein for locking the stem 12 which is secured to the junction 13 and is thinner than the holding portion 11 in facility of being stretched into the cavity of the mouth. The leading end of the stem 12 includes a holding member 30 for the dental floss and a locating member 20 for securing the holding member 30.

Figure 4:
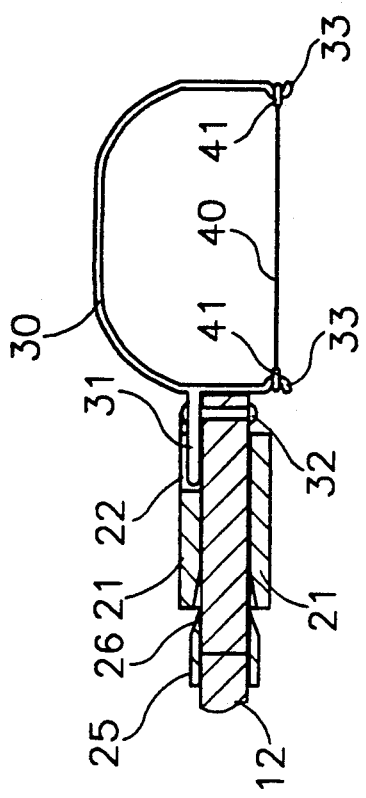
FIG. 4 is a local side exploded view of locating member and holding member for the dental floss.
Figure 3:
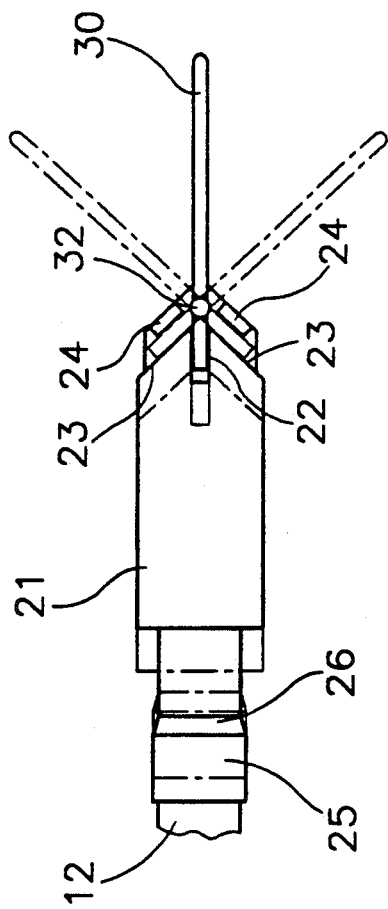
FIG. 3 is a perspective view showing the operation of locating member and holding member for the dental floss of this invention.
Figure 5:
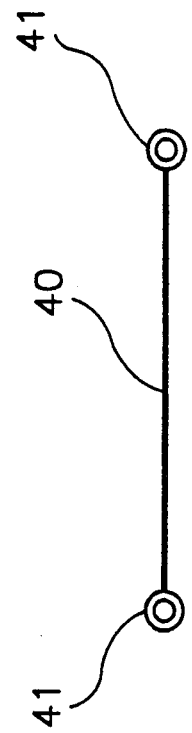
FIG. 5 is a top view of the dental floss having a circular holding member.

Referring to FIGS. 2, 3 and 4 the holding member 30 is mounted at the leading end of the stem 12 by virtue of a pin 32 which is made from steel wire or elastic material such as plastic to resemble a "U" shape and one side of which has a handle 31 and both ends of the open side of "U" shaped body have a portion 33 respectively for mounting the dental floss 40. Referring to FIG. 4 the stationary portion 33 resembles a hook shape and both ends of the dental floss 40 are secured together with a stationary member 41 which resembles a circular shape (as FIG. 5). The two stationary members 41 of the dental floss 40 are cased in the stationary portion 33 to secure the dental floss 40 with the function of its own tension force; when the leading and rear ends of the holding member 30 are tightly held the dental floss 40 would become relaxed to allow for removal and replacement.

Except for the method as shown in FIG. 4, there remain some other methods for quick mounting the dental floss 40 on the holding member 30 in order to meet the purpose of quick replacement. Referring to FIGS. 6 and 7 a groove 34 can be cut in the center of the hook-shaped portion 33 in parallel to the holding member 30 for the dental floss and both ends of the dental floss 40 can be respectively secured together with a stationary member 42 resembling a solid block (as FIG. 8) for hooking the two stationary members 42 into the portion 33 so that the dental floss 40 will enter the groove 34 and therefore the dental floss 40 is secured thereof.

In order to secure the holding member 30 for the dental floss the holder 10 has a locating member 20 thereon for locating the holding member 30 at different angles of inclination as shown in FIGS. 3 and 4. The locating member 20 of this invention includes two stop blocks 24 which angularly arranged and located at the leading end of the stem 12 and a slide buckle 21 slidably cased at the rear side of the stop blocks 24 on the stem 12. Wherein the leading end of the slide buckle 21 has two mutually inclined bevels 23 which are fitted the stop blocks 24 each other, and a groove 22 which can be set in together with the handle 31 at the final end of the holding member 30 for securing the holding member 30 at a parallel position to the holder 10. When the floss head 30 is desired for a angle of inclination the user may push the slide buckle 21 backward with the thumb to cause the groove 22 disengaging with the handle 31 of the holding member 30 so that the holding member 30 can swing left-handed and right-handed; when the holding member 30 is turned left-handed or right-handed at an angle of inclination and the slide buckle 21 is pushed forward with the thumb to cause the bevel 23 pushing the handle 31 tightly against the stop blocks 24 whereby the holding member 30 for the dental floss can be located left-handed or right-handed at an angle of inclination.

Figure 10:
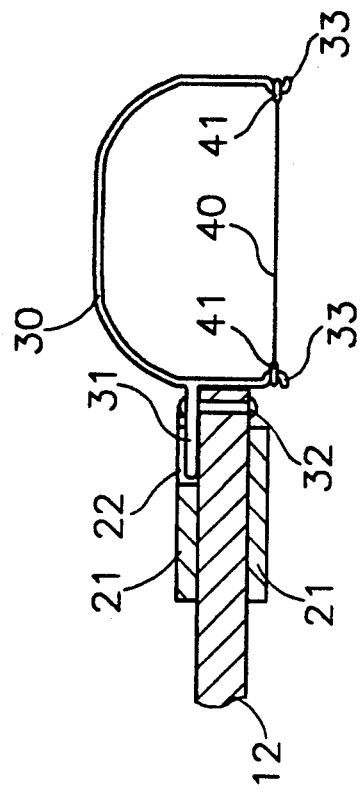
FIG. 10 is a side exploded view of an embodiment of this invention without stop member.
Figure 9:
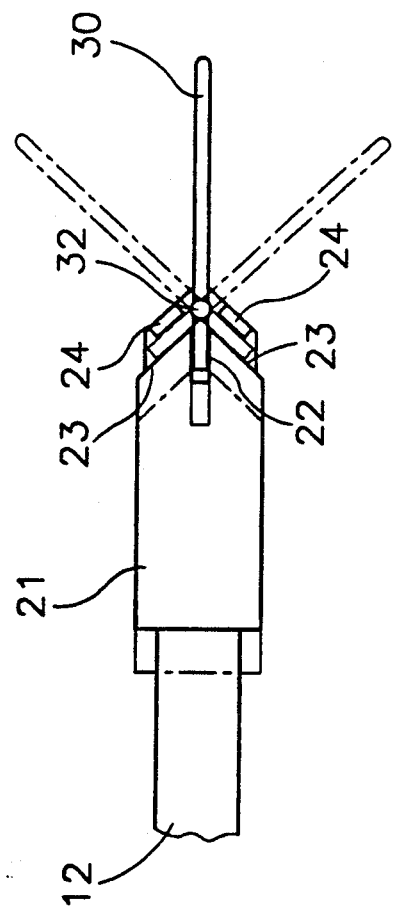
FIG. 9 is a top view of an embodiment of this invention without stop member.

In order to get the slide buckle 21 thoroughly secured to the holding member 30 there is a stop member 25 mounted on the stem 12 for preventing the slide buckle 21 from sliding backward as shown in FIGS. 2, 3 and 4. The stop member 25 is slidably cased on the stem 12 and located at the rear side of the slide buckle 21. The leading end of the stop member 25 has a reducing end 26 and the rear end on the inner hole of the slide buckle 21 has an expanding end 27. When the slide buckle 21 is pushed forward for securing the holding member 30 the stop member 25 can be pushed forward with the thumb for inserting its reducing end 26 into the expanding end 27 at the rear end of the slide buckle 21 whereby the slide buckle 21 is secured. When the stop member is pushed backward to cause the reducing end 26 disengaging with the expanding end 27 of the slide buckle 21 whereby the slide buckle 21 can be released backward. In addition there remain some other methods for securing the slide buckle 21 as shown in FIGS. 9 and 10 wherein the slide buckle 21 will be limited to slide as a result of reducing its space between with the stem 12, or when in use the user may hold back the slide buckle 21 with the fingers in order to meet the purpose of effectively securing the slide buckle 21 to the holding member 30 for the dental member 30.

The advantages of this invention for use include: (1) the holding member for the dental floss is operative to clean up the deep portion in the cavity of the mouth with the design of change in the angles (2) dental floss can be disposed after use without necessity of disposing the whole device so as to minimize the waste.

What is claimed is:

1. A dental floss holder comprising:
   a) a holder portion defining a chamber for storing dental floss therein;
   b) a locating member attached to and extending from an end of the holder portion, the location member having a distal end portion;
   c) a generally "U"-shaped dental floss holding member having a pair of legs adapted to removably attach thereto a segment of dental floss such that the dental floss extends between the pair of legs and a locking pin extending outwardly from one of the pair of legs;
   d) attaching means to permanently attach the dental floss holding member to the distal end of the locating member such that the dental floss holding member may pivot with respect to the locating member;
   e) a plurality of stop blocks located adjacent to the distal end of the locating member; and,
   f) a slide member slidably attached to the locating member so as to be movable between a first position wherein the dental floss holding member is pivotable with respect to the locating member and a second position wherein the locking pin is held between a stop block and the slide member so as to hold the dental floss holding member stationary with respect to the locating member.

2. The dental floss holder of claim 1 further comprising at least one groove defined by the slide member and adapted to receive therein the locking pin when the slide member is in its second position.

3. The dental floss holder of claim 1 wherein each of the pair of legs has a generally hook-shaped end portion adapted to engage elements on a dental floss segment so as to releasably attach the dental floss segment to the dental floss holding member.

4. The dental floss holder of claim 1 wherein each of the pair of legs has an end portion defining slot adapted to receive therein an end of a dental floss segment.

* * * * *